United States Patent

Znaiden et al.

[11] Patent Number: 5,552,147
[45] Date of Patent: Sep. 3, 1996

[54] PETROLEUM JELLY WITH ALPHA HYDROXY CARBOXYLIC ACIDS

[75] Inventors: Alexander P. Znaiden, Trumbull; Michael C. Cheney, Fairfield; Walter Rose, New Haven, all of Conn.

[73] Assignee: Chesebrough-Pond's USA Co., Division of Conopco, Inc., Greenwich, Conn.

[21] Appl. No.: 428,760

[22] Filed: Apr. 25, 1995

[51] Int. Cl.⁶ .............................................. A61K 7/48
[52] U.S. Cl. .................. 424/401; 424/642; 514/847; 514/78; 514/558; 514/729; 514/739
[58] Field of Search .............................. 424/401, 317, 424/279, 283, 642; 514/847

[56] References Cited

U.S. PATENT DOCUMENTS

| 4,021,572 | 5/1977 | Van Scott et al. | 424/317 |
| 4,105,782 | 8/1978 | Yu et al. | 424/283 |
| 4,105,783 | 8/1978 | Yu et al. | 424/283 |
| 4,234,599 | 11/1980 | Van Scott et al. | 424/279 |
| 4,424,234 | 1/1984 | Alderson et al. | 424/317 |
| 4,760,096 | 7/1988 | Sakai et al. | 514/847 |
| 5,091,171 | 2/1992 | Yu et al. | 424/642 |
| 5,310,556 | 5/1994 | Ziegler | 424/401 |
| 5,434,144 | 7/1995 | Kasting et al. | |

FOREIGN PATENT DOCUMENTS

WO90/01323  2/1990  WIPO.

*Primary Examiner*—Thurman K. Page
*Assistant Examiner*—Sharon Howard
*Attorney, Agent, or Firm*—Milton L. Honig

[57] ABSTRACT

A cosmetic composition is provided that includes a $C_2$–$C_{22}$ α-hydroxy carboxylic acid or salt thereof dispersed within petroleum jelly with the aid of a phosphatide. Additional components may include a sterol and a $C_{10}$–$C_{22}$ fatty acid.

9 Claims, No Drawings

PETROLEUM JELLY WITH ALPHA HYDROXY CARBOXYLIC ACIDS

BACKGROUND OF THE INVENTION

1. Field of the Invention

The invention relates to cosmetic compositions whose major component is petroleum jelly incorporating $\alpha$-hydroxy carboxylic acids and salts thereof.

2. The Related Art

Petroleum jelly is one of the oldest skin treatment products still in commerce today. For over 100 years, the Chesebrough Company and its successors have sold the substance under the brand, Vaseline®. There is good reason for the longevity of this product. Its occlusive and healing properties render this product especially efficacious against dry and damaged skin.

Within recent years, $\alpha$-hydroxy carboxylic acids have gained prominence as one of the truly effective skin actives. Reports of these materials are found in U.S. Pat. No. 4,021,572, U.S. Pat. No. 4,234,599, U.S. Pat. No. 4,105,782 and U.S. Pat. No. 4,105,783 listing Yu and Van Scott as inventors. Other properties of these substances include their action against age spots, wrinkles and other signs of aging. See U.S. Pat. No. 5,091,171 (Yu et al.) and U.S. Pat. No. 4,424,234 (Alderson et al.).

Delivery of $\alpha$-hydroxy carboxylic acids in a vehicle such as petroleum jelly appears to present potential for even higher levels of effectiveness than previously found with aqueous cream and lotion vehicles. $\alpha$-Hydroxy carboxylic acids and their salts are unfortunately not readily soluble or dispersible in petroleum jelly. Systems are required which can aid dispersion of these hydrophilic substances into petroleum jelly.

Accordingly, it is an object of the present invention to provide cosmetic compositions having $\alpha$-hydroxy carboxylic acids or salts thereof uniformly dispersed or solubilized within petroleum jelly.

Another object of the present invention is to provide cosmetic compositions with skin healing, moisturizing, anti-aging, anti-wrinkling, skin lightening and other improved functional activities.

These and other objects of the present invention will become more readily apparent from consideration of the following summary and detailed description.

SUMMARY OF THE INVENTION

A cosmetic composition is provided that includes:

(i) from about 50% to about 98% by weight of petroleum jelly;

(ii) from about 0.01 to about 20% by weight of a $C_2$–$C_{20}$ $\alpha$-hydroxy carboxylic acid or salt thereof; and (iii) from about 0.1 to about 10% by weight of a phosphatide.

DETAILED DESCRIPTION OF THE INVENTION

Now it has been found that a cosmetic composition wherein petroleum jelly is the main component and vehicle can be formulated with the aid of a phosphatide to microdisperse therein a $C_2$–$C_{22}$ $\alpha$-hydroxy carboxylic acid or salt thereof. Enhanced dispersion can be achieved when the phosphatide is accompanied by other lipid components such as a fatty acid and a sterol. The lipid system prevents phase separation and maintains the cosmetic product in an extended state of stability.

Accordingly, a first essential element of the present invention is that of petroleum jelly. Amounts of this material may range from about 50% to about 98%, preferably from about 60% to about 95%, optimally from about 75% to about 90% by weight.

A second essential element of the present invention is that of a $C_2$–$C_{22}$ $\alpha$-hydroxy carboxylic acid or salt thereof. Illustrative of these substances are glycolic, lactic, malic, tartaric acids and mixtures thereof. Salts of these acids may be based upon cations such as alkalimetal, alkaline earth metal, ammonium, and $C_2$–$C_{20}$ alkanolammonium cations. Amounts of the $\alpha$-hydroxy carboxylic acid or salt may range from about 0.1 to about 20%, preferably from about 0.5 to about 10%, optimally from about 1 to about 5% by weight.

A further essential element of the present invention is that of a phosphatide. Most preferred is lecithin. Amounts of this material may range from about 0.1 to about 10%, preferably from about 0.5 to about 8%, optimally from about 2 to about 5% by weight.

Additional lipids may be included in compositions of the present invention. Particularly effective are $C_{10}$–$C_{22}$ fatty acids. Suitable fatty acids include lauryl, myristyl, cetyl, palmityl, oleoyl, stearic, isostearic and behenyl acids. Amounts of this substance may range from about 0.1 to about 20%, preferably from about 0.5 to about 10%, optimally from about 1% to about 6% by weight.

Other particularly effective lipids are the sterols. Illustrative sterols are those selected from soy sterol, ergosterol, stigmasterol, cholesterol, sitosterol and combinations thereof. Amounts of this material may range from about 0.1 to about 20%, preferably from about 0.5 to about 10%, optimally from about 1 to about 5% by weight.

Although compositions according to the present invention may be anhydrous, they usually will contain water in amounts from 0 to 15%, preferably from about 0.8 to about 10%, optimally from about 1 to about 8%, especially from about 4 to about 6% by weight.

Beyond the aforementioned components, the present invention may also include other ingredients typically found in cosmetic formulations. Among these ingredients are emollients, humectants, thickeners, preservatives, fragrances and vitamins.

Emollients may be selected from materials such as $C_8$–$C_{30}$ fatty alcohols, triglyceride oils, silicone oils and a variety of esters. Amounts of the emollients may range from about 0.5 to about 20%, preferably from about 1 to about 10%, optimally from about 2 to about 8% by weight. Illustrative emollients are stearyl alcohol, cetyl alcohol, isopropyl palmitate, isopropyl myristate, lanolin, sunflower oil, evening primrose oil, soybean oil, dimethicone, cyclomethicone, dimethicone copolyol and dimethyl polysiloxane.

Thickeners may be selected from such materials as crosslinked polyacrylates available under the Carbopol® trademark, celluloses such as sodium carboxymethylcellulose, hydroxyethylcellulose, hydroxypropylcellulose and methyl cellulose, and natural gums such as xanthan, carrageenan and pectin gums. Most preferred are the crosslinked polyacrylates, especially Carbopol 934® available from the B. F. Goodrich Company.

Powdered thickeners may be such materials as chalk, talc, Fullers earth, kaolin, starch, colloidal silica, smectites clays, montmorillonite clays and chemically modified magnesium aluminum silicates.

Among the preservatives useful are methyl paraben, propyl paraben, EDTA salts, potassium sorbate, potassium benzoate and DMDM hydantoin.

Cosmetic compositions of the present invention may also contain vitamin ingredients such as Vitamin A palmitate, Vitamin E acetate, Niacin, Vitamin C and combinations thereof.

Emulsifiers may also be useful for purposes of the present invention. These emulsifiers may be alkoxylated $C_8$–$C_{30}$ fatty acids and fatty alcohols. Examples of such materials are polyoxyethylene (4) lauryl ether, polyoxyethylene (8) monostearate, polyoxyethylene (10) cetyl ether and polyoxyethylene (20) stearyl ether. A particularly preferred emulsifier is Myreth-3-Myristate (CTFA name) available commercially as Cetiol 1414-E®.

The following examples will more fully illustrate select embodiments of this invention. All parts, percentages and proportions referred to herein and in the appended claims are by weight of the total composition unless otherwise stated.

EXAMPLE 1

A series of experiments were conducted to evaluate compatibility of potassium lactate in petroleum jelly. Table I outlines formulations and phase stability results.

The foregoing description and Examples illustrate selected embodiments of the present invention. In light thereof, various modifications will be suggested to one skilled in the art, all of which are within the spirit and purview of this invention.

What is claimed is:

1. A cosmetic composition comprising:
   (i) from about 50% to about 98% by weight of petroleum jelly;
   (ii) from about 0.01 to about 20% by weight of a $C_2$–$C_{20}$ α-hydroxy carboxylic acid or salt thereof;
   (iii) from about 0.1 to about 10% by weight of a phosphatide; and
   (iv) from 0 to 15% by weight of water.

2. A cosmetic composition according to claim 1 further comprising from about 0.1 to about 10% by weight of a sterol.

3. A cosmetic composition according to claim 1 further comprising from about 0.1 to about 10% by weight of a $C_{10}$–$C_{22}$ fatty acid.

4. A cosmetic composition according to claim 1 further comprising from about 4 to about 10% by weight of water.

TABLE I

| COMPONENT | FORMULA (WT. %) | | | | | | | | | | | |
| --- | --- | --- | --- | --- | --- | --- | --- | --- | --- | --- | --- | --- |
| | 1 | 2 | 3 | 4 | 5 | 6 | 7 | 8 | 9 | 10 | 11 | 12 |
| Petroleum Jelly | 89.75 | 89.75 | 89.75 | 89.75 | 89.75 | 89.75 | 81.75 | 83.75 | 83.75 | 83.75 | 85.75 | 85.75 |
| Potassium Lactate (66% Aqueous Solution) | 8.25 | 8.25 | 8.25 | 0.25 | 8.25 | 8.25 | 8.25 | 8.25 | 8.25 | 8.25 | 8.25 | 8.25 |
| Lecithin | 2.00 | — | — | — | — | — | 4.00 | 4.00 | 4.00 | 4.00 | — | 4.00 |
| Soy Sterol | — | 2.00 | — | — | — | — | 4.00 | 4.00 | — | 4.00 | 4.00 | 2.00 |
| Stearic Acid | — | 2.00 | — | 2.00 | — | — | 2.00 | — | 4.00 | — | 2.00 | — |
| Sunflower Seed Oil | — | 2.00 | 2.00 | — | — | — | — | — | — | — | — | — |
| Cholesterol | — | 2.00 | — | — | 2.00 | — | — | — | — | — | — | — |
| Sorbitan Monooleate | — | 2.00 | — | — | — | 2.00 | — | — | — | — | — | — |
| PHASE STABILITY | unstable | separation | unstable | unstable | unstable | unstable | stable | stable | stable | stable | unstable | unstable |

Based on the results in Table I, it appears that lecithin at levels of about 4% provides stability to the potassium lactate in petroleum jelly.

EXAMPLE 2

The following formulas illustrate typical compositions according to the present invention.

TABLE II

| COMPONENT | FORMULA (WT. %) | | | | | |
| --- | --- | --- | --- | --- | --- | --- |
| | 13 | 14 | 15 | 16 | 17 | 18 |
| Petroleum Jelly | 50 | 95 | 98 | 75 | 85 | 85 |
| Ammonium Glycolate | 10 | — | 0.01 | 20 | 5 | 1 |
| Glycolic Acid | 10 | 3 | — | — | — | — |
| Alpha-Hydroxycaprylic Acid | 1 | — | — | — | — | — |
| Lecithin | 5 | 2 | 0.10 | 3 | 4 | 10 |
| Cholesterol | 5 | — | 0.10 | — | — | 1 |
| Polyoxyethylene (20) Stearyl Ether | 2 | — | 1.79 | 2 | 2 | 2 |
| Water | 7 | — | — | — | 4 | 1 |

5. A cosmetic composition according to claim 1 wherein the phosphatide is lecithin.

6. A cosmetic composition according to claim 1 where the phosphatide is present from about 4 to about 10% by weight.

7. A cosmetic composition according to claim 1 wherein the petroleum jelly is present from about 60% to about 95%.

8. A cosmetic composition according to claim 1 wherein the petroleum jelly is present from about 75% to about 90%.

9. A method for treating skin to improve a functional activity selected from the group consisting of skin healing, moisturizing, anti-aging, anti-wrinkling, skin lightening and combinations thereof, by applying to the skin a cosmetic composition comprising from about 50% to 98% by weight of petroleum jelly, from about 0.01 to about 20% by weight of a $C_2$–$C_{20}$ α-hydroxycarboxylic acid or salt thereof, and from 0 to 15% by weight of water.

* * * * *